United States Patent
Lee et al.

(10) Patent No.: US 11,653,636 B2
(45) Date of Patent: May 23, 2023

(54) METHOD OF MAKING A RAT MODEL OF RETINAL DEGENERATION AND RAT MODEL MADE THEREBY

(71) Applicants: UNIVERSITY OF ULSAN FOUNDATION FOR INDUSTRY COOPERATION, Ulsan (KR); THE ASAN FOUNDATION, Seoul (KR)

(72) Inventors: Joo Yong Lee, Seoul (KR); In Jeoung Baek, Seoul (KR); Young Hoon Sung, Seoul (KR)

(73) Assignees: UNIVERSITY OF ULSAN FOUNDATION FOR INDUSTRY COOPERATION, Ulsan (KR); THE ASAN FOUNDATION, Seoul (KR)

( * ) Notice: Subject to any disclaimer, the term of this patent is extended or adjusted under 35 U.S.C. 154(b) by 691 days.

(21) Appl. No.: 16/686,024

(22) Filed: Nov. 15, 2019

(65) Prior Publication Data
US 2021/0144976 A1    May 20, 2021

(51) Int. Cl.
| | | |
|---|---|---|
| *C12N 15/00* | (2006.01) | |
| *A01K 67/027* | (2006.01) | |
| *G01N 33/00* | (2006.01) | |
| *A61K 49/00* | (2006.01) | |
| *C12N 15/85* | (2006.01) | |

(52) U.S. Cl.
CPC ...... *A01K 67/0276* (2013.01); *A61K 49/0008* (2013.01); *C12N 15/8509* (2013.01); *A01K 2217/075* (2013.01); *A01K 2227/105* (2013.01); *A01K 2267/0306* (2013.01); *C12N 2015/8536* (2013.01)

(58) Field of Classification Search
None
See application file for complete search history.

(56) References Cited

U.S. PATENT DOCUMENTS

| | | | | |
|---|---|---|---|---|
| 6,225,291 B1 * | 5/2001 | Lewin | ............ | A61P 27/02 435/456 |
| 7,595,430 B2 * | 9/2009 | Jayakrishna | ..... | C07K 14/70596 800/18 |
| 11,434,527 B2 | 9/2022 | Kang et al. | | |
| 2015/0079047 A1 * | 3/2015 | Farber | ............ | A61P 27/02 435/325 |
| 2019/0203207 A1 * | 7/2019 | Tsang | ............ | C07K 14/47 |
| 2021/0115505 A1 | 4/2021 | Kang et al. | | |

FOREIGN PATENT DOCUMENTS

| | | |
|---|---|---|
| KR | 10-2010-0121710 | 11/2010 |
| KR | 10-2017-0137354 | 12/2017 |

OTHER PUBLICATIONS

Tsang (Human Mutation, 2007, vol. 28, vol. 28, No. 3, p. 243-254).*
Yeo (ARVO Annual Meeting, Jul. 2019).*
Yeo (Ophthalmol. Vis. Sci. Apr. 4, 2019, vol. 60, No. 5, p. 1519-1526).*
Carter-Dawson (Invest. Ophthalmol. Visual Sci., 1978, p. 489-498).*
DiCarlo et al., "CRISPR-Cas Genome Surgery in Ophthalmology," Translational Vision Science & Technology (2017) 6(3): Article 13, 13 pgs.
Kim et al., "Generation of knockout mice by Cpf1-mediated gene targeting," Nat Biotechnol. Aug. 2016;34(8):808-10.
Muradov et al., "Atypical retinal degeneration 3 in mice is caused by defective PDE6B pre-mRNA splicing," Vision Res. (2012) 57: 1-8.
Zhu et al., "An efficient genotyping method for genome-modified animals and human cells generated with CRISPR/Cas9 system," Sci Rep. (2014) 4: 6420.

* cited by examiner

*Primary Examiner* — Michael C Wilson
(74) *Attorney, Agent, or Firm* — Morrison & Foerster LLP

(57) ABSTRACT

The present invention relates to a Pde6b-deficient animal model of retinal degeneration produced by engineered endonucleases, and a method for producing the same. In the animal model of retinal degeneration according to the present invention, only a specific target gene can be removed using engineered endonucleases, so that mutagenesis can be stably achieved. In addition, it is possible to produce a congenital animal model through genetic manipulation at the embryonic stage rather than through acquired factors, which allows for production of an animal model that uniformly exhibits symptoms of the disease in question without being influenced by other factors.

10 Claims, 19 Drawing Sheets
Specification includes a Sequence Listing.

| Name | Position | Strand | Sequence | PAM | Specificity Score |
|---|---|---|---|---|---|
| Pde6b-CR1 | 99 | -1 | AGGGCTCAGCTTCTTCTCAA (SEQ ID NO: 1) | TTTC (SEQ ID NO: 13) | 47.6382168 |
| Pde6b-CR2 | 457 | -1 | TCATCTCTTGGTCTGAGCC (SEQ ID NO: 2) | TTTA (SEQ ID NO: 14) | 47.7193067 |

FIG. 1B

T7-AsPde6b_CR1  GAAATTAATACGACTCACTATAGGGTAATTTCTACTCTTGTAGATAGGGCTCAGCTTCTTCTCAA (SEQ ID NO: 3)
T7-AsPde6b_CR2  GAAATTAATACGACTCACTATAGGGTAATTTCTACTCTTGTAGATTCATCTTCTTGGTCTGAGCC (SEQ ID NO: 4)

FIG. 1C

>T7 top strand
GAAATTAATACGACTCACTATAGGG (SEQ ID NO: 5)
>Anti-T7-AsPde6b_CR1
TTGAGAAGAAGCTGAGCCCTATCTACAAGAGTAGAAATTACCCTATAGTGAGTCGTATTAATTTC (SEQ ID NO: 6)
>Anti-T7-AsPde6b_CR2
GGCTCAGACCAAGAAGAATCTACAAGAGTAGAAATTACCCTATAGTGAGTCGTATTAATTTC (SEQ ID NO: 7)

FIG. 1D

| Primer name | Sequence (5'->3') | Template strand | Length | Start | Stop | Tm | GC% |
|---|---|---|---|---|---|---|---|
| rPde6b_F1 | CAGTGAGGAACAAGTACGCAG (SEQ ID NO: 8) | Plus | 21 | 39 | 59 | 58.94 | 52.38 |
| rPde6b_F2 | ATGGGAACCCCACCTTTGCC (SEQ ID NO: 9) | Plus | 20 | 68 | 87 | 62.75 | 60 |
| rPde6b_R1 | CTACACGGTAGCCGGAGATCA (SEQ ID NO: 10) | Minus | 21 | 524 | 504 | 61.08 | 57.14 |
| rPde6b_R2 | ATGCAGAACACTACTCTACACGG (SEQ ID NO: 11) | Minus | 23 | 539 | 517 | 60.12 | 47.83 |

FIG. 2A

|              | rPde6b_R1 | rPde6b_R2 |
|--------------|-----------|-----------|
| rPde6b_F1    | 486 bp    | 501 bp    |
| rPde6b_F2    | 457 bp    | 472 bp    |

FIG. 2B

Touchdown PCR

| | | |
|---|---|---|
| 95°C | 3:00 | |
| 95°C | 0:30 | |
| 68°C (-1°C/cycle) | 0:30 | 10 cycle |
| 72°C | 0:45 | |
| 95°C | 0:30 | |
| 58°C | 0:30 | 25 cycle |
| 72°C | 0:45 | |
| 72°C | 5:00 | |
| 16°C | forever | |

FIG. 2C

|  | Sequence | | SEQ ID NO |
|---|---|---|---|
|  | L D G N P T F A H Q Y F E K K L S P E N V A G | | SEQ ID NO: 15 |
| WT | TGGATGGGAACCCCACCTTTGCCCACCAATACTTTTGAGAAGAAGCTGAGTCCTGAAAATGTGGCAGGGG | | SEQ ID NO: 16 |
| #26 | TGGATGGGAACCCCACCTTTGCCCACCAATACTTTGAGAAGAAGCTGAGTCCTGAAAATGTGGCAGGGG | WT (21/23) | SEQ ID NO: 17 |
|  | TGGATGGGAACCCCACCTTTGCCCACCAATATG---------AGCTGTGCCTGAAAATGTGGCAGGGG | -11+3 (2/23) | SEQ ID NO: 18 |
| #26-7 | TGGATGGGAACCCCACCTTTGCCCACCAATACTTTGAGAAGAAGCTGAGTCCTGAAAATGTGGCAGGGG | WT | SEQ ID NO: 19 |
| #26-10 | TGGATGGGAACCCCACCTTTGCCCACCAATATG---------AGCTGTGCCTGAAAATGTGGCAGGGG | -11+3 | SEQ ID NO: 20 |
|  | TGGATGGGAACCCCACCTTTGCCCACCAATACTTTGAGAAGAAGCTGAGTCCTGAAAATGTGGCAGGGG | WT | SEQ ID NO: 21 |
|  | TGGATGGGAACCCCACCTTTGCCCACCAATATG---------AGCTGTGCCTGAAAATGTGGCAGGGG | -11+3 | SEQ ID NO: 22 |
| #33 | TGGATGGGAACCCCACCTTTGCCCACCAATACTTTGAGAAGAAGCTGAGTCCTGAAAATGTGGCAGGGG | WT (7/9) | SEQ ID NO: 23 |
|  | TGGATGGGAACCCCACCTTTGCCCACCAATA-----------AGCTGAGCCTGAAAATGTGGCAGGGG | -11 (2/9) | SEQ ID NO: 24 |
| #33-2 | TGGATGGGAACCCCACCTTTGCCCACCAATACTTTGAGAAGAAGCTGAGTCCTGAAAATGTGGCAGGGG | WT | SEQ ID NO: 25 |
| #33-3 | TGGATGGGAACCCCACCTTTGCCCACCAATA-----------AGCTGAGCCTGAAAATGTGGCAGGGG | -11 | SEQ ID NO: 26 |
|  | TGGATGGGAACCCCACCTTTGCCCACCAATACTTTGAGAAGAAGCTGAGTCCTGAAAATGTGGCAGGGG | WT | SEQ ID NO: 27 |
|  | TGGATGGGAACCCCACCTTTGCCCACCAATA-----------AGCTGAGCCTGAAAATGTGGCAGGGG | -11 | SEQ ID NO: 28 |
| #33-9 | TGGATGGGAACCCCACCTTTGCCCACCAATACTTTGAGAAGAAGCTGAGTCCTGAAAATGTGGCAGGGG | WT | SEQ ID NO: 29 |
|  | TGGATGGGAACCCCACCTTTGCCCACCAATA-----------AGCTGAGCCTGAAAATGTGGCAGGGG | -11 | SEQ ID NO: 30 |
| #33-12 | TGGATGGGAACCCCACCTTTGCCCACCAATACTTTGAGAAGAAGCTGAGTCCTGAAAATGTGGCAGGGG | WT | SEQ ID NO: 31 |
|  | TGGATGGGAACCCCACCTTTGCCCACCAATA-----------AGCTGAGCCTGAAAATGTGGCAGGGG | -11 | SEQ ID NO: 32 |

FIG. 3B

SEQUENCE LISTING

<160> NUMBER OF SEQ ID NOS: 34

<210> SEQ ID NO 1
<211> LENGTH: 20
<212> TYPE: DNA
<213> ORGANISM: Artificial
<220> FEATURE:
<223> OTHER INFORMATION: Pde6b-CR1

<400> SEQUENCE: 1
agggctcagc ttcttctcaa                    20

<210> SEQ ID NO 2
<211> LENGTH: 20
<212> TYPE: DNA
<213> ORGANISM: Artificial
<220> FEATURE:
<223> OTHER INFORMATION: Pde6b-CR2

<400> SEQUENCE: 2
tcatcttctt ggtctgagcc                    20

<210> SEQ ID NO 3

-continued

```
<211> LENGTH: 65
<212> TYPE: DNA
<213> ORGANISM: Artificial
<220> FEATURE:
<223> OTHER INFORMATION: T7-AsPde6b_CR1

<400> SEQUENCE: 3
gaaattaata cgactcacta tagggtaatt tctactcttg tagatagggc tcagcttctt    60
ctcaa                                                                65

<210> SEQ ID NO 4
<211> LENGTH: 65
<212> TYPE: DNA
<213> ORGANISM: Artificial
<220> FEATURE:
<223> OTHER INFORMATION: T7-AsPde6b_CR2

<400> SEQUENCE: 4
gaaattaata cgactcacta tagggtaatt tctactcttg tagattcatc ttcttggtct    60
gagcc                                                                65

<210> SEQ ID NO 5
<211> LENGTH: 25
<212> TYPE: DNA
<213> ORGANISM: Artificial
<220> FEATURE:
<223> OTHER INFORMATION: T7 top strand

<400> SEQUENCE: 5
gaaattaata cgactcacta taggg                                          25

<210> SEQ ID NO 6
<211> LENGTH: 65
<212> TYPE: DNA
<213> ORGANISM: Artificial
<220> FEATURE:
<223> OTHER INFORMATION: Anti-T7-AsPde6b_CR1

<400> SEQUENCE: 6
ttgagaagaa gctgagccct atctacaaga gtagaaatta ccctatagtg agtcgtatta    60
atttc                                                                65

<210> SEQ ID NO 7
<211> LENGTH: 65
<212> TYPE: DNA
<213> ORGANISM: Artificial
<220> FEATURE:
<223> OTHER INFORMATION: Anti-T7-AsPde6b_CR2

<400> SEQUENCE: 7
ggctcagacc aagaagatga atctacaaga gtagaaatta ccctatagtg agtcgtatta    60
atttc                                                                65

<210> SEQ ID NO 8
<211> LENGTH: 21
<212> TYPE: DNA
<213> ORGANISM: Artificial
<220> FEATURE:
<223> OTHER INFORMATION: rPde6b_F1

<400> SEQUENCE: 8
cagtgaggaa caagtacgca g                                              21
```

-continued

<210> SEQ ID NO 9
<211> LENGTH: 20
<212> TYPE: DNA
<213> ORGANISM: Artificial
<220> FEATURE:
<223> OTHER INFORMATION: rPde6b_F2

<400> SEQUENCE: 9
atgggaaccc cacctttgcc                                              20

<210> SEQ ID NO 10
<211> LENGTH: 21
<212> TYPE: DNA
<213> ORGANISM: Artificial
<220> FEATURE:
<223> OTHER INFORMATION: rPde6b_R1

<400> SEQUENCE: 10
ctacacggta gccggagatc a                                            21

<210> SEQ ID NO 11
<211> LENGTH: 23
<212> TYPE: DNA
<213> ORGANISM: Artificial
<220> FEATURE:
<223> OTHER INFORMATION: rPde6b_R2

<400> SEQUENCE: 11
atgcagaaca ctactctaca cgg                                          23

<210> SEQ ID NO 12
<211> LENGTH: 69
<212> TYPE: DNA
<213> ORGANISM: Artificial
<220> FEATURE:
<223> OTHER INFORMATION: coding region of exon 1 of Pde6b gene

<400> SEQUENCE: 12
ctggatggga accccacctt tgcccaccaa tactttgaga agaagctgag ccctgaaaat    60
gtggcaggg                                                          69

<210> SEQ ID NO 13
<211> LENGTH: 4
<212> TYPE: DNA
<213> ORGANISM: Artificial
<220> FEATURE:
<223> OTHER INFORMATION: PAM

<400> SEQUENCE: 13 tttc                                                                4

<210> SEQ ID NO 14
<211> LENGTH: 4
<212> TYPE: DNA
<213> ORGANISM: Artificial
<220> FEATURE:
<223> OTHER INFORMATION: PAM

<400> SEQUENCE: 14 ttta                                                                4

<210> SEQ ID NO 15
<211> LENGTH: 23
<212> TYPE: PRT
<213> ORGANISM: Artificial
<220> FEATURE:

```
<223> OTHER INFORMATION: WT

<400> SEQUENCE: 15

Leu Asp Gly Asn Pro Thr Phe Ala His Gln Tyr Phe Glu Lys Lys Leu
1               5                   10                  15

Ser Pro Glu Asn Val Ala Gly
            20

<210> SEQ ID NO 16
<211> LENGTH: 69
<212> TYPE: DNA
<213> ORGANISM: Artificial
<220> FEATURE:
<223> OTHER INFORMATION: WT

<400> SEQUENCE: 16
tggatgggaa ccccaccttt gcccaccaat actttgagaa gaagctgagc cctgaaaatg    60
tggcagggg                                                             69

<210> SEQ ID NO 17
<211> LENGTH: 69
<212> TYPE: DNA
<213> ORGANISM: Artificial
<220> FEATURE:
<223> OTHER INFORMATION: #26 WT (21/23)

<400> SEQUENCE: 17
tggatgggaa ccccaccttt gcccaccaat actttgagaa gaagctgagc cctgaaaatg    60
tggcagggg                                                             69

<210> SEQ ID NO 18
<211> LENGTH: 69
<212> TYPE: DNA
<213> ORGANISM: Artificial
<220> FEATURE:
<223> OTHER INFORMATION: #26 -11+3 (2/23)
<220> FEATURE:
<221> NAME/KEY: misc_feature
<222> LOCATION: (35)..(42)
<223> OTHER INFORMATION: n is a deleted nucleotide.

<400> SEQUENCE: 18
tggatgggaa ccccaccttt gcccaccaat attcnnnnnn nnagctgagc cctgaaaatg    60
tggcagggg                                                             69

<210> SEQ ID NO 19
<211> LENGTH: 69
<212> TYPE: DNA
<213> ORGANISM: Artificial
<220> FEATURE:
<223> OTHER INFORMATION: #26-7 WT

<400> SEQUENCE: 19
tggatgggaa ccccaccttt gcccaccaat actttgagaa gaagctgagc cctgaaaatg    60
tggcagggg                                                             69

<210> SEQ ID NO 20
<211> LENGTH: 69
<212> TYPE: DNA
<213> ORGANISM: Artificial
<220> FEATURE:
<223> OTHER INFORMATION: #26-7 -11+3
<220> FEATURE:
<221> NAME/KEY: misc_feature
```

```
<222> LOCATION: (35)..(42)
<223> OTHER INFORMATION: n is a deleted nucleotide.

<400> SEQUENCE: 20
tggatgggaa ccccaccttt gcccaccaat attcnnnnnn nnagctgagc cctgaaaatg    60
tggcagggg                                                            69

<210> SEQ ID NO 21
<211> LENGTH: 69
<212> TYPE: DNA
<213> ORGANISM: Artificial
<220> FEATURE:
<223> OTHER INFORMATION: #26-10 WT

<400> SEQUENCE: 21
tggatgggaa ccccaccttt gcccaccaat actttgagaa gaagctgagc cctgaaaatg    60
tggcagggg                                                            69

<210> SEQ ID NO 22
<211> LENGTH: 69
<212> TYPE: DNA
<213> ORGANISM: Artificial
<220> FEATURE:
<223> OTHER INFORMATION: #26-10 -11+3
<220> FEATURE:
<221> NAME/KEY: misc_feature
<222> LOCATION: (35)..(42)
<223> OTHER INFORMATION: n is a deleted nucleotide.

<400> SEQUENCE: 22
tggatgggaa ccccaccttt gcccaccaat attcnnnnnn nnagctgagc cctgaaaatg    60
tggcagggg                                                            69

<210> SEQ ID NO 23
<211> LENGTH: 69
<212> TYPE: DNA
<213> ORGANISM: Artificial
<220> FEATURE:
<223> OTHER INFORMATION: #33 WT (7/9)

<400> SEQUENCE: 23
tggatgggaa ccccaccttt gcccaccaat actttgagaa gaagctgagc cctgaaaatg    60
tggcagggg                                                            69

<210> SEQ ID NO 24
<211> LENGTH: 69
<212> TYPE: DNA
<213> ORGANISM: Artificial
<220> FEATURE:
<223> OTHER INFORMATION: #33 -11 (2/9)
<220> FEATURE:
<221> NAME/KEY: misc_feature
<222> LOCATION: (32)..(42)
<223> OTHER INFORMATION: n is a deleted nucleotide.

<400> SEQUENCE: 24
tggatgggaa ccccaccttt gcccaccaat annnnnnnnn nnagctgagc cctgaaaatg    60
tggcagggg                                                            69

<210> SEQ ID NO 25
<211> LENGTH: 69
<212> TYPE: DNA
<213> ORGANISM: Artificial
<220> FEATURE:
```

<223> OTHER INFORMATION: #33-2 WT

<400> SEQUENCE: 25
tggatgggaa cccaccttt gcccaccaat actttgagaa gaagctgagc cctgaaaatg    60
tggcagggg                                                            69

<210> SEQ ID NO 26
<211> LENGTH: 69
<212> TYPE: DNA
<213> ORGANISM: Artificial
<220> FEATURE:
<223> OTHER INFORMATION: #33-2 -11
<220> FEATURE:
<221> NAME/KEY: misc_feature
<222> LOCATION: (32)..(42)
<223> OTHER INFORMATION: n is a deleted nucleotide.

<400> SEQUENCE: 26
tggatgggaa cccaccttt gcccaccaat annnnnnnnn nnagctgagc cctgaaaatg    60
tggcagggg                                                            69

<210> SEQ ID NO 27
<211> LENGTH: 69
<212> TYPE: DNA
<213> ORGANISM: Artificial
<220> FEATURE:
<223> OTHER INFORMATION: #33-3 WT

<400> SEQUENCE: 27
tggatgggaa cccaccttt gcccaccaat actttgagaa gaagctgagc cctgaaaatg    60
tggcagggg                                                            69

<210> SEQ ID NO 28
<211> LENGTH: 69
<212> TYPE: DNA
<213> ORGANISM: Artificial
<220> FEATURE:
<223> OTHER INFORMATION: #33-3 -11
<220> FEATURE:
<221> NAME/KEY: misc_feature
<222> LOCATION: (32)..(42)
<223> OTHER INFORMATION: n is a deleted nucleotide.

<400> SEQUENCE: 28
tggatgggaa cccaccttt gcccaccaat annnnnnnnn nnagctgagc cctgaaaatg    60
tggcagggg                                                            69

<210> SEQ ID NO 29
<211> LENGTH: 69
<212> TYPE: DNA
<213> ORGANISM: Artificial
<220> FEATURE:
<223> OTHER INFORMATION: #33-9 WT

<400> SEQUENCE: 29
tggatgggaa cccaccttt gcccaccaat actttgagaa gaagctgagc cctgaaaatg    60
tggcagggg                                                            69

<210> SEQ ID NO 30
<211> LENGTH: 69
<212> TYPE: DNA
<213> ORGANISM: Artificial
<220> FEATURE:
<223> OTHER INFORMATION: #33-9 -11

```
<220> FEATURE:
<221> NAME/KEY: misc_feature
<222> LOCATION: (32)..(42)
<223> OTHER INFORMATION: n is a deleted nucleotide.

<400> SEQUENCE: 30
tggatgggaa ccccacctttt gcccaccaat annnnnnnnn nnagctgagc cctgaaaatg      60
tggcagggg                                                               69

<210> SEQ ID NO 31
<211> LENGTH: 69
<212> TYPE: DNA
<213> ORGANISM: Artificial
<220> FEATURE:
<223> OTHER INFORMATION: #33-12 WT

<400> SEQUENCE: 31
tggatgggaa ccccacctttt gcccaccaat actttgagaa gaagctgagc cctgaaaatg      60
tggcagggg                                                               69

<210> SEQ ID NO 32
<211> LENGTH: 69
<212> TYPE: DNA
<213> ORGANISM: Artificial
<220> FEATURE:
<223> OTHER INFORMATION: #33-12 -11
<220> FEATURE:
<221> NAME/KEY: misc_feature
<222> LOCATION: (32)..(42)
<223> OTHER INFORMATION: n is a deleted nucleotide.

<400> SEQUENCE: 32
tggatgggaa ccccacctttt gcccaccaat annnnnnnnn nnagctgagc cctgaaaatg      60
tggcagggg                                                               69

<210> SEQ ID NO 33
<211> LENGTH: 23
<212> TYPE: PRT
<213> ORGANISM: Artificial
<220> FEATURE:
<223> OTHER INFORMATION: coding region of exon 1 of Pde6b gene

<400> SEQUENCE: 33

Leu Asp Gly Asn Pro Thr Phe Ala His Gln Tyr Phe Glu Lys Lys Leu
 1               5                  10                  15

Ser Pro Glu Asn Val Ala Gly
             20

<210> SEQ ID NO 34
<211> LENGTH: 20
<212> TYPE: DNA
<213> ORGANISM: Artificial
<220> FEATURE:
<223> OTHER INFORMATION: rPde6b_R5

<400> SEQUENCE: 34
gacgctctct tgcatgtcct                                                   20
```

METHOD OF MAKING A RAT MODEL OF RETINAL DEGENERATION AND RAT MODEL MADE THEREBY

INCORPORATION BY REFERENCE OF SEQUENCE LISTING

The present application is being filed along with a Sequence Listing in electronic format. The Sequence Listing is provided as a file entitled 717572001000SeqList.txt, created Nov. 15, 2019, which is 8.8 kilobytes in size. The information in the electronic format of the Sequence Listing is incorporated by reference in its entirety.

BACKGROUND OF THE INVENTION

1. Field of the Invention

The present invention relates to a Pde6b-deficient animal model of retinal degeneration produced by engineered endonucleases, and a method for producing the same.

2. Description of the Related Art

The retina refers to the innermost layer of nerve tissue covering the eye. When light having entered the eye passes through the inner retinal layer and is detected by retinal visual cells, the visual cells convert light information into electrical information, which, in turn, passes through inner retinal layer cells and is delivered, through the optic nerve, to the brain where visual information is recognizable.

The retina may be divided into thin transparent membranes having different thicknesses depending on locations; and the central part of the retina is subdivided into fovea centralis, parafovea, and perifovea. Among these, the fovea centralis is clinically referred to as the macula. More specifically, the retina may be histologically composed of ten layers in a superficial to deep direction of the eye. The ten constituent layers are, respectively, retinal pigment epithelium, photoreceptor layer, outer limiting membrane, outer nuclear layer, outer plexiform layer, inner nuclear layer, inner plexiform layer, ganglion cell layer, nerve fiber layer, and internal limiting membrane. Among these, the photoreceptor layer is a light-sensing part and consists of two types of visual cells, that is, cone cells and rod cells. On average, the human retina is known to have about 100 million rod cells and about 6 million cone cells. In particular, the retina has special regions such as optic disk and macula, and visual information is received through the visual stimulus recognition function of the retina. In consideration of these facts, retinal damage may lead to severe vision problems. Therefore, various therapeutic methods have been studied to improve symptoms caused by such retinal degeneration and damage, and production of an animal model is indispensable, for example, for identifying effects of improving clinical symptoms in such studies.

In the course of producing an animal model, a method capable of producing a disease-induced animal model, in which an experimental animal is exposed to an environment causing a target disease or is administered a compound, has been used in various disease models. However, in this case, such an animal model may be greatly influenced by the induced acquired disease in terms of complications and individual differences. Thus, attention has been paid to a method for producing an animal model, which is induced to innately develop a target disease, by manipulating genetic information.

To this end, a technique called genome editing may be used to induce deletion or overexpression of specific genes, thereby freely editing genetic information of living organisms. The genome editing technique has the advantage that as such a technique is used to alter genetic information of animals including humans, plants, or microorganisms, its application range is dramatically expanding. In particular, among others, engineered endonucleases are a molecular tool designed to specifically cut only the desired genetic information, and play a key role in the genome editing technique. Various cases have been reported on techniques for making such Engineered endonucleases. Korean Patent No. 10-1842014 discloses that Cpf1 endonucleases are used to induce deletion of Prkdc gene, thereby producing a transgenic immunodeficient mouse. In addition, study results, obtained by using the CRISPR-Cas system, on genes that may affect eye development have been known (DiCarlo, James E., et al. Translational vision science & technology 6.3 (2017): 13-13).

Accordingly, the present inventors have made attempts to produce an animal model in which gene knockout is specifically induced through this Engineered endonucleases, and as a result, have produced Pde6b gene knockout rats using the CRISPR-Cpf1. The present inventors have found that the rats significantly show findings of retinal degeneration, and thus can be used as an animal model of ocular diseases caused by retinal degeneration, thereby completing the present invention.

SUMMARY OF THE INVENTION

An object of the present invention is to provide an animal model of retinal degeneration and a method for producing the same.

Another object of the present invention is to provide a method for screening a therapeutic agent for retinal degeneration, using the animal model of retinal degeneration.

In order to achieve the above objects, the present invention provides a method for producing an animal model of retinal degeneration, comprising a step of inducing Pde6b gene knockout.

In a preferred embodiment of the present invention, the step of inducing Pde6b gene knockout may be carried out through the following steps i) to iii):

i) generating crRNA and Cpf1 mRNA which recognize the Pde6b gene;

ii) injecting the crRNA and the Cpf1 mRNA into an embryo of an animal model; and iii) transplanting the embryo into a foster mother to produce a Pde6b-deficient animal. In a preferred embodiment of the present invention, the animal may be a mammal other than a human. Specifically, the mammal may be a rodent, and may preferably be a rat.

In a preferred embodiment of the present invention, the retinal degeneration may be any one or more selected from the group consisting of retinal pigment degeneration, angioid streak, drusen, and macular degeneration.

In addition, the present invention provides a Pde6b-deficient animal model of retinal degeneration.

In a preferred embodiment of the present invention, the Pde6b gene knockout may be induced by engineered endonucleases.

In addition, the present invention provides a method for screening a prophylactic or therapeutic drug for retinal degeneration, comprising the following steps i) and ii):

i) subjecting a Pde6b-deficient animal model of the present invention to treatment with a candidate drug before or after retinal degeneration occurs; and ii) identifying whether the animal model treated with the candidate drug develops retinal degeneration or identifying progress of symptoms of retinal degeneration therein as compared with an untreated control, in a case where the animal model is subjected to treatment with the candidate drug before retinal degeneration occurs in step i); or comparing the animal model treated with the candidate drug with an untreated control, to identify improvement in symptoms of retinal degeneration, in a case where the animal model is subjected to treatment with the candidate drug after retinal degeneration occurs in step i).

In a preferred embodiment of the present invention, the improvement in symptoms of retinal degeneration in step ii) may be any one or more selected from the group consisting of improved retinal vascular morphology, increased retinal single-layer thickness, increased electroretinogram amplitude, and increased cell number in retinal tissue.

In a preferred embodiment of the present invention, the retinal degeneration may be any one or more selected from the group consisting of retinal pigment degeneration, angioid streak, drusen, and macular degeneration.

Accordingly, the present invention provides a Pde6b-deficient animal model of retinal degeneration and a method for producing the same. In the animal model of retinal degeneration according to the present invention, only a specific target gene may be removed using engineered endonucleases and this may be expected to be inherited through germline transmission, so that mutagenesis can be stably achieved. In addition, it is possible to produce a congenital animal model through genetic manipulation at the embryonic stage rather than through acquired factors, which allows for production of an animal model that uniformly exhibits symptoms of the disease in question without being influenced by other factors.

BRIEF DESCRIPTION OF THE DRAWINGS

FIGS. 1A to 1D illustrate a preparation process of CRISPR-Cpf1 for removing Pde6b gene.

FIGS. 2A to 2D illustrate design of genotyping primers for identifying Pde6b gene knockout, and genotyping results obtained by using the same.

FIGS. 3A to 3C illustrate results obtained by sequencing the Pde6b gene in Pde6b gene knockout rats.

DESCRIPTION OF THE PREFERRED EMBODIMENTS

Figure 1A:
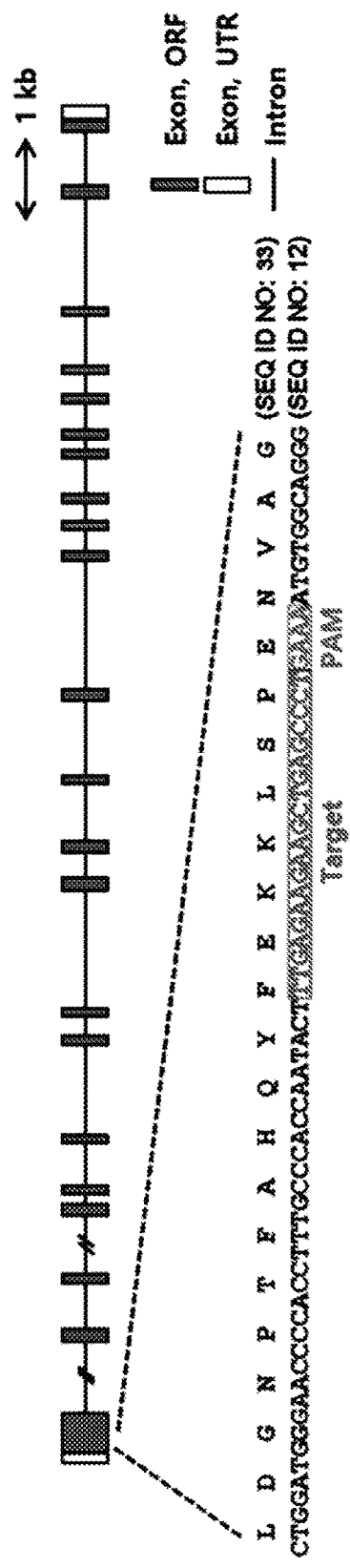

Hereinafter, the present invention will be described in detail.

The present invention provides a method for producing an animal model of retinal degeneration, comprising a step of inducing Pde6b gene knockout.

In addition, the present invention provides an animal model of retinal degeneration, produced according to the above method.

As used herein, the term "animal model" refers to an animal having a disease that is morphologically very similar to a human disease. In studying human diseases, a diseased animal model is significant due to physiological or genetic similarities between humans and animals. In studying diseases, diseased animal models for biomedicine provide research materials for various causes, pathogenesis, and diagnosis of diseases; allow for identification of genes related to diseases through studies with the diseased animal models; allow for understanding of interactions between genes; and make it possible to obtain basic data, through actual efficacy and toxicity tests of newly developed drug candidates, for determining whether such drug candidates can be put to practical use.

In the "method for producing an animal model of retinal degeneration" of the present invention, for the step of inducing Pde6b gene mutation, it is preferable that the Pde6b gene is mutated using the engineered endonucleases prepared using the methods known in Korean Laid-open Patent Publication No. 10-2017-0137354 and Kim et al. Nature Biotechnology 34.8 (2016): 808. More specifically, it is more preferred that the step of inducing Pde6b gene knockout is carried out through, but not limited to, the following steps i) to iii):

i) generating crRNA and Cpf1 mRNA which recognize the Pde6b gene;

ii) injecting the crRNA and the Cpf1 mRNA into an embryo of an animal model; and iii) transplanting the embryo into a foster mother to produce a Pde6b-deficient animal.

In the method of the present invention, the technique using engineered endonucleases may be understood, by those skilled in the art, as a technique mainly used for knock-out research tools, through which the function of a gene is eliminated by recognizing and cutting a desired DNA sequence to cause damage, and allowing mutagenesis, which causes changes in the number and type of nucleotide sequence, to occur in the course of repairing the damage. The engineered endonucleases is a technique of introducing a mutation into a DNA nucleotide sequence to alter the genetic code itself, and is different from gene knockdown in which RNA interference (RNAi) is used to target RNA. miRNA, siRNA, or shRNA used in RNAi technique binds to transcribed mRNA to degrade it or inhibit translation thereof, thereby decreasing a gene expression level. Therefore, the engineered endonucleases is preferred because it can induce a target gene knockout in a more sensitive and effective manner than knocking down the target gene.

As used herein, the terms "deletion", "knock-out", and "deficiency" all mean abolishing the function of a particular gene and are used interchangeably in the present specification.

The method for producing an animal model of retinal degeneration of the present invention comprises knocking out a particular gene, such as Pde6b gene, using various Cpf1 orthologs which are class 2 single RNA-guide endonucleases.

In the method of the present invention, the crRNA and Cpf1 mRNA in step i) may be prepared by methods known in the art.

The crRNA targets the coding region of exon 1 of the Pde6b gene as illustrated in FIG. 1A. For example, the crRNA may be prepared with reference to the method disclosed in Kim et al. Nature Biotechnology 34.8 (2016): 808. Specifically, in order to avoid possible off-target cleavages, the present inventors selected a CRISPR RNA sequence in the rat Pde6b gene that exhibits three or more mismatches and at least one mismatch residing in the 5' PAM-proximal region.

Regarding the Cpf1, two proteins used by *Acidaminococcus* and Lachnospiraceae mediate efficient genome editing in human cells. Therefore, in the method of the present invention, for the Cpf1 gene, Cpf1 ortholog gene derived from *Acidaminococcus* sp. or Lachnospiraceae bacterium may be used. More specifically, Cpf1 ortholog gene derived from *Acidaminococcus* sp. BV3L6 (AsCpf1) or Lachnospiraceae bacterium N D2006 (LbCpf1) may be used. The Cpf1 is prepared as mRNA for injection into rats, and the Cpf1 mRNA may be prepared by linearizing a vector containing a nucleotide sequence encoding Cpf1, and then subjecting the resultant to an in vitro transcription process.

In the present invention, step ii) of injecting the crRNA and the Cpf1 mRNA into an embryo of an animal model may be carried out, for example, by a simple method in which the crRNA and the Cpf1 mRNA are mixed and the mixture is injected into the cytoplasm of a fertilized egg.

The crRNA and the Cpf1 mRNA may be injected into a rat embryo by methods commonly known in the art. For example, microinjection, electroporation, liposome-mediated transfer method, and retrovirus-mediated transfer method may be applied therefor.

In step ii), the embryo for injection may be obtained by the following process. First, superovulation is induced in female SD rats (5 to 6 weeks old) by injection with 30 to 40 IU pregnant mare serum gonadotropin (PMSG; Sigma-Aldrich Corp., St. Louis, Mo., USA) and 40 to 100 IU human chorionic gonadotropin (hCG; Daesung Microbiological Labs Co., Ltd., Gyeounggi, Republic of Korea) at 48- to 50-hour intervals. The superovulated female rats are crossed with SD stud male rats, and 1-cell stage embryos are collected from the oviducts 6 to 14 hours after fertilization.

Subsequently, using a microinjector, for example, 100 ng/ml of crRNA and 50 ng/ml of Cpf1 mRNA may be co-injected into the cytoplasm of pronuclear stage embryos.

In the present invention, step iii) is a step of transplanting the embryo, into which the crRNA and the Cpf1 mRNA have been injected, into the oviduct of a pseudo-pregnant foster mother to produce a Pde6b-deficient animal, in which, for example, the embryo after injection with the crRNA and the Cpf1 mRNA may be incubated for 2 to 24 hours in a 37° C. incubator and transplanted, at the 1-cell or 2-cell stage, into the foster mother.

The incubation is performed according to known methods. For example, a suitable medium may be developed for incubation of animal cells, in particular, mammalian cells, or any available medium may be used which may be prepared in the laboratory with appropriate ingredients required for animal cell growth, such as anabolic carbon, nitrogen, and/or micronutrients.

The medium may be any basal medium suitable for animal embryo growth. Non-limiting examples of the basal medium generally used for incubation include M2, M16, m-RECM, Modification of medium SOM (KSOM), Human Tubal Fluid (HTF), Minimum Essential Medium (MMEM), Dulbecco modified Eagle Medium (DMEM), Roswell Park Memorial Institute Medium (RPMI), and Keratinocyte Serum Free Medium (K-SFM). In addition, any medium used in the art may be used without limitation. Preferably, the medium may be selected from the group consisting of M2 (SIGMA), M16 (SIGMA), m-RECM (COSMOBIO), KSOM (COSMOBIO), HTF (Irvine Scientific), α-MEM medium (GIBCO), K-SFM medium, DMEM medium (Welgene), MCDB 131 medium (Welgene), IMEM medium (GIBCO), DMEM/F12 medium, PCM medium, M199/F12 (mixture) (GIBCO), and MSC expansion medium (Chemicon).

To this basal medium may be added anabolic sources of carbon, nitrogen, and micronutrients, of which non-limiting examples include serum sources, growth factors, amino acids, antibiotics, vitamins, reducing agents, and/or sugar sources.

It will be apparent to one of ordinary skill in the art that the most suitable medium may be selected or prepared by combination so that incubation is appropriately performed with known methods. In addition, it is apparent that incubation may be performed while adjusting conditions such as suitable incubation environment, time, and temperature, based on common knowledge in the art.

The method of the present invention may further comprise step iv) of screening for Pde6b gene mutations in the newborn animals produced in step iii), to select founder animals ($F_0$) with mutations that are expected to lack the function of the Pde6b gene.

Identification of the mutations may be accomplished by genotyping, sequencing, or the like, and may also be accomplished by other methods known in the art.

Mutations caused by engineered endonucleases may be detected by a variety of methods including, for example, mismatch-sensitive T7 endonuclease I (T7E1) or Surveyor nuclease assay, RFLP, capillary electrophoresis of fluorescence-labeled PCR products, dideoxy sequencing, and deep sequencing.

In an embodiment of the present invention, founder (F0) rats with a targeted mutation were screened by using PCR primers (rPde6b_F1: SEQ ID NO: 8 and rPde6b_R1: SEQ ID NO: 10). Mutant alleles were identified by Sanger sequencing of cloned PCR products (generated by using a T-Blunt PCR Cloning Kit [SolGent Co., Ltd., Daejeon, Republic of Korea]).

In addition, in order to establish Pde6b knockout animal lines, the method of the present invention may further comprise step v) of crossing mutant animal founders ($F_0$) with Pde6b deficient alleles with wild-type animals, to obtain heterozygous Pde6b knockout animals ($F_1$); and step vi) of crossing the heterozygous Pde6b knockout male animals with the heterozygous Pde6b knockout female animals, to obtain homozygous Pde6b knockout animals ($F_2$).

In the method of the present invention, in a case where, in the $F_1$ generation, an animal with the same Pde6b gene loss-of-function mutation as observed in the founders ($F_0$) is found, it is said that germline transmission has occurred. Germline-transmitted mutants are expected to continuously represent the mutations in a reliable manner at later generations.

In an embodiment of the present invention, for routine PCR genotyping, a primer pair (rPde6b_F2: SEQ ID NO: 9; rPde6b_R5: SEQ ID NO: 34) that produced a short PCR product (173 bp in wild-type rats) was used to detect deletion with a frameshift mutation in the knockout allele.

Figure 3A:
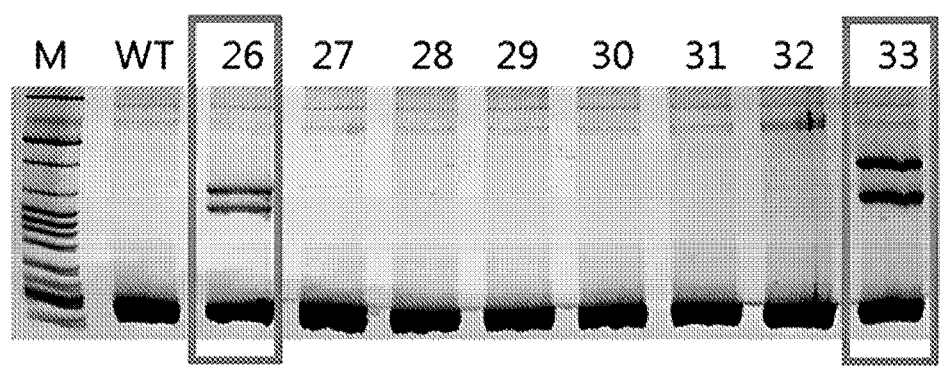
Figure 3C:
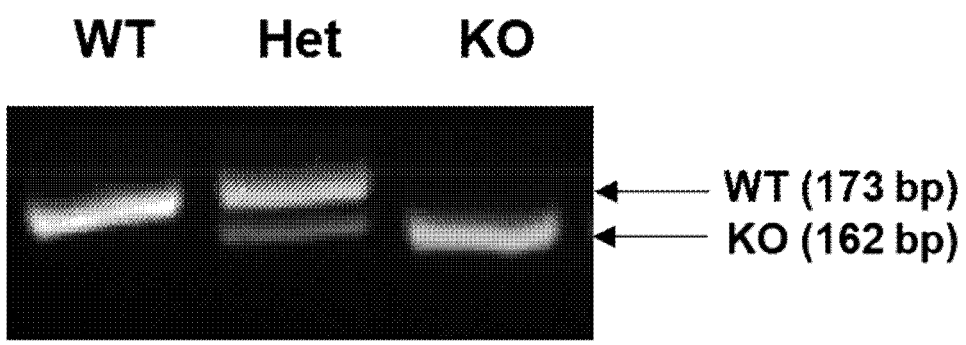
Figure 4:
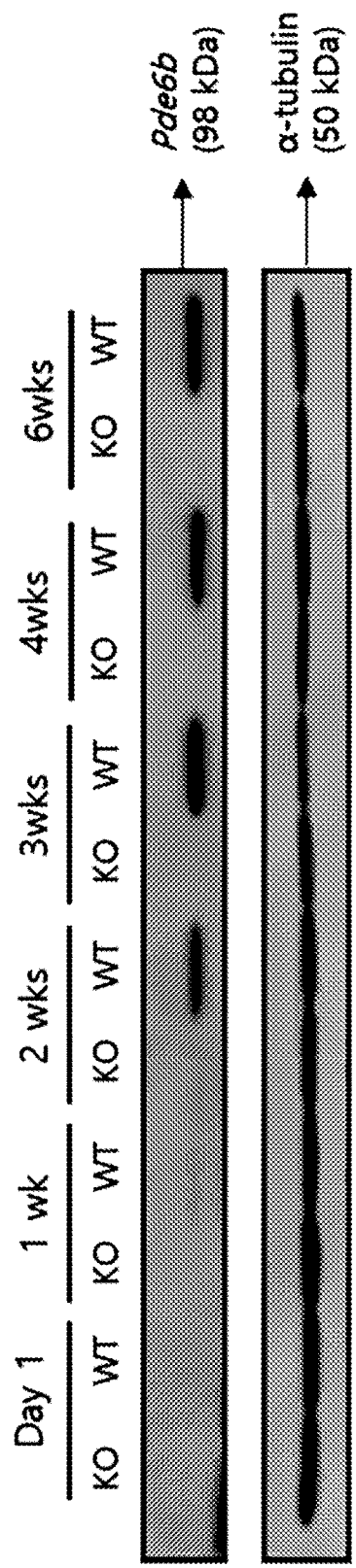
FIG. 4 illustrates results obtained by identifying, with Western blotting, expression of Pde6b protein in the retina of wild type rats and Pde6b knockout rats.

In an embodiment of the present invention, after identifying the frameshift mutations of founder rats #26 and #33, a Pde6b-mutant rat line with an 11-bp deletion was established (FIGS. 3B and 3C). Western blot analysis identified deficiency of Pde6b protein in the homozygous mutant retina, indicating successful generation of Pde6b-deficient rats with Cpf1-mediated gene targeting (FIG. 4).

Fundoscopy was carried out to identify clinical phenotype of Pde6b knockout rats produced by the method of the present invention. As a result, as identified in FIG. 5, the retinal appearance of the Pde6b knockout rats produced by the method of the present invention was distinguished from that of wild-type rats. Specifically, the fundus photographs of the wild-type rats showed radial patterns of arterioles and venules, whereas the Pde6b knockout rats showed irregular radial patterns of retinal vessels with attenuated retinal arterioles. At 8 weeks of postnatal age, the Pde6b knockout rats showed a thinned retina, resulting in prominent choroidal vessels.

In the method of the present invention, the animal model of retinal degeneration is preferably a mammal other than a human. More specifically, the animal model is more preferably, but is not limited to, a rodent. For example, in a case where the animal model of retinal degeneration of the present invention is a rodent, the rodent is most preferably a rat or a mouse. The rat model has greater translational relevance than previously established mouse models due to its similarities to humans in many biological aspects. Therefore, in the present invention, rats are used to generate an animal model of retinal degeneration.

In the method of the present invention, the retinal degeneration is preferably any one or more selected from, but not limited to, the group consisting of retinal pigment degeneration, angioid streak, drusen, and macular degeneration; and any disease that may be caused by damage to the retina or developmental inhibition thereof may be included without limitation so long as the disease is within the scope recognized by those skilled in the art.

The Pde6b knockout rats produced by the method of the present invention may be used to screen potential drugs for the prevention or treatment of various diseases associated with retinal degeneration. Screening for useful drugs includes, for example, a step of administering a candidate drug to rats over a range of doses, and a step of analyzing, at various time points, effects of the drug in the disease to be evaluated.

Accordingly, the present invention provides a method for screening a prophylactic or therapeutic drug for retinal degeneration, comprising the following steps i) and ii):

i) subjecting a Pde6b-deficient animal model of the present invention to treatment with a candidate drug before or after retinal degeneration occurs; and ii) identifying whether the animal model treated with the candidate drug develops retinal degeneration or identifying progress of symptoms of retinal degeneration therein as compared with an untreated control, in a case where the animal model is subjected to treatment with the candidate drug before retinal degeneration occurs in step i); or comparing the animal model treated with the candidate drug with an untreated control, to identify improvement in symptoms of retinal degeneration, in a case where the animal model is subjected to treatment with the candidate drug after retinal degeneration occurs in step i).

In the method for screening a prophylactic or therapeutic drug for retinal degeneration of the present invention, the prophylactic or therapeutic drug refers to a substance exerting all actions that alleviate the patient's health condition, such as preventing or delaying onset of disease and improving symptoms.

In the method for screening a prophylactic or therapeutic drug for retinal degeneration of the present invention, the candidate drug includes candidate drugs in all routes of administration. For example, drugs for parenteral administration such as intraocular administration and for oral administration may be screened. For a dosage of the drug, the optimal dosage may be appropriately determined by making a comprehensive decision based on conditions such as nature of drug, kind of subject to be administered, and the subject's age or body weight. Conditions such as time of administration and number of administrations may be appropriately set depending on nature of drug, purposes of test and evaluation, and the like. In addition, these methods may be used to quantify effects of drugs, so that the effects of drugs are quantitatively determined.

In the method for screening a prophylactic or therapeutic drug for retinal degeneration of the present invention, as a subject for comparison with the animal with retinal degeneration of the present invention, an untreated control, which is a Pde6b-deficient animal model not treated with a candidate drug, may be used. Normal control rats in which Pde6b deficiency is not induced may also be used as a control. More specifically, the progress of symptoms of retinal degeneration in step ii) may be identified by comparison with an untreated control and/or a normal control in terms of, but not limited to, retinal vascular morphology, retinal single-layer thickness, electroretinogram amplitude, and cell number in retinal tissue. In addition, the improvement in symptoms of retinal degeneration in step ii) is preferably, but is not limited to, any one or more selected from the group consisting of improved retinal vascular morphology, increased retinal single-layer thickness, increased electroretinogram amplitude, and increased cell number in retinal tissue.

In the method of the present invention, the retinal degeneration is preferably any one or more selected from, but not limited to, the group consisting of retinal pigment degeneration, angioid streak, drusen, and macular degeneration; and any disease that may be caused by damage to the retina or developmental inhibition thereof may be included without limitation so long as the disease is within the scope recognized by those skilled in the art.

Additionally, the Pde6b knockout animal model of the present invention may be useful for studying effects of Pde6b gene mutation. Embodiments of the Pde6b knockout animal model and progeny thereof of the present invention will also have various uses depending on additional transgenes that can be expressed and/or knockout constructs they may contain.

Hereinafter, the present invention will be described in more detail by way of examples. These examples are given to merely illustrate the present invention, and it is obvious to one of ordinary skill in the art that the scope of the present invention is not interpreted to be limited by these examples.

Example 1

Preparation for Pde6b-Deficient Rat Generation

<1-1> Construction of Engineered Endonucleases Specific to Pde6b Gene

In order to produce a Pde6b-deficient animal model, engineered endonucleases capable of specifically removing the PDE6B gene were prepared.

Specifically, the engineered endonucleases may be those that can perform in rats using AsCpf1. Based on known results, the engineered endonucleases, CRISPR-Cpf1, were constructed (Kim, Yongsub, et al. Nature Biotechnology 34.8 (2016): 808). To this end, two CRISPR RNAs (Pde6b-CR1: SEQ ID NO: 1; and Pde6b-CR2: SEQ ID NO: 2) were first selected using Benching software (https://benchling- .com/; in the public domain) (FIG. 1B). Based on this, in vitro transcription templates (T7-AsPde6b_CR1: SEQ ID NO: 3; and T7-AsPde6b_CR2: SEQ ID NO: 4) were designed (FIG. 1C), and DNA oligomers (FIG. 1D: SEQ ID NOS: 5 to 7) capable of complementarily binding thereto were custom made and used for in vitro transcription. Cpf1 mRNA was generated using pcDNA3.1-hAsCpf1 (Addgene #69982), and CRISPR RNA was generated in the same manner as previously reported (Kim, Yongsub, et al. Nature Biotechnology 34.8 (2016): 808).

<1-2> Selection of Genotyping Primers

Genotyping primers were selected for the production of Pde6b knockout rats. According to a known experimental method, primer sequences were designed to produce a PCR product of heteroduplex DNA (Zhu, Xiaoxiao, et al. Scientific Reports 4 (2014): 6420). As illustrated in FIG. 2A, for primer sequences, two forward primers (rPde6b_F1: SEQ ID NO: 8; rPde6b_F2: SEQ ID NO: 9) and three reverse primers (rPde6b_R1: SEQ ID NO: 10; rPde6b_R2: SEQ ID NO: 11, rPde6b_R5: SEQ ID NO: 34) were produced (FIG. 2A, data not shown for rPde6b_R5). In a case where PCR is performed by combining the respective forward and reverse primers, it was expected that the resulting products have sizes as summarized in FIG. 2B (FIG. 2B, data not shown for rPde6b_R5). Then, touchdown PCR was performed according to the PCR conditions as summarized in FIG. 2C. The PCR product of heteroduplex DNA was separated by electrophoresis, and a variant identification method was performed thereon (data not shown for rPde6b_R5).

Figure 2D:
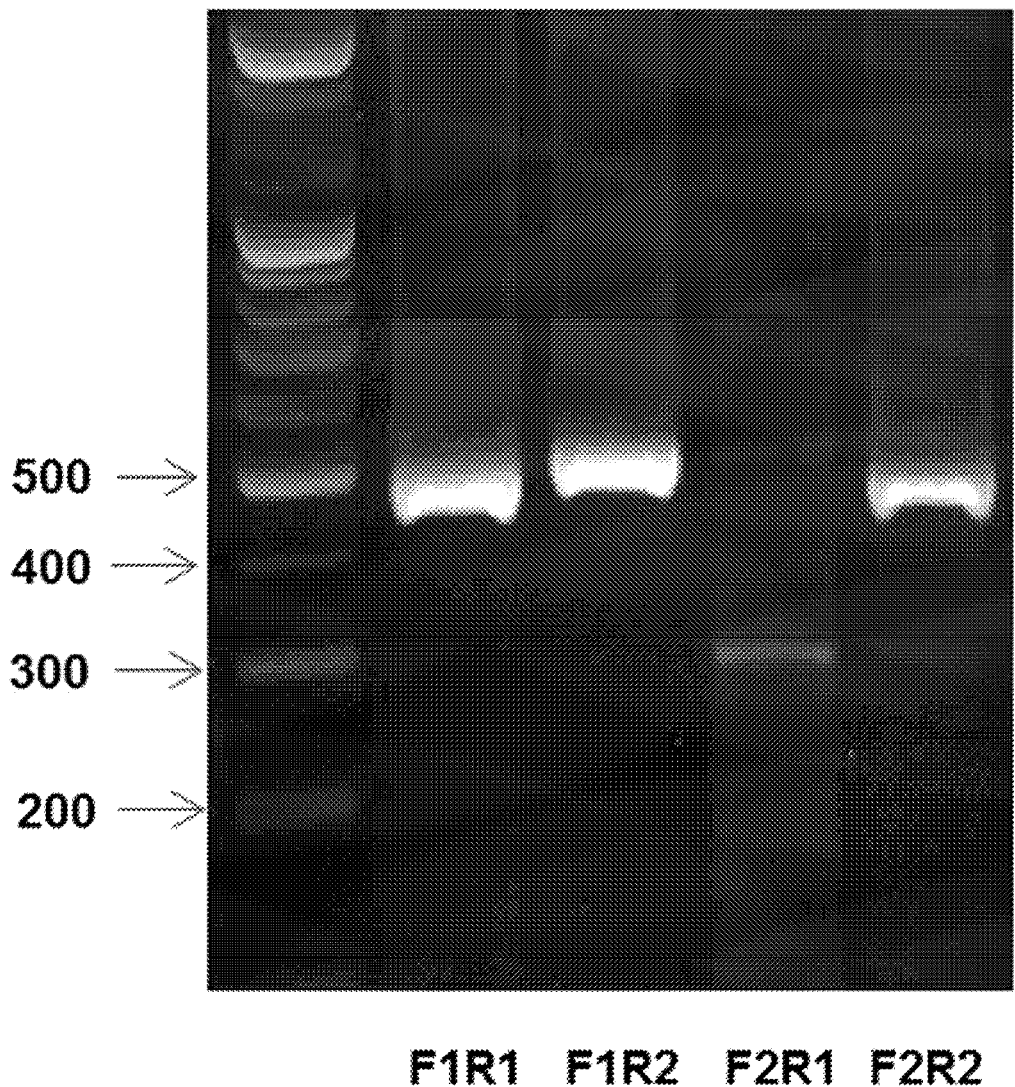

As a result, as illustrated in FIG. 2D, it was identified that the PCR product is amplified. Based on this, in the subsequent genotyping process, the rPde6b_F1 and rPde6b_R1 primer pair was used for the screening of $F_0$ generation. In genotyping PCR, rPde6b_F2: SEQ ID NO: 9 and rPde6b_R5: SEQ ID NO: 34 (GACGCTCTCTTG-CATGTCCT) were used.

Example 2

Production of Rat Model of Retinal Degeneration

<2-1> Environment Under which Animal Experiment is Conducted

First, all animal experiments performed in the present invention are performed while complying with the guidelines related to animal experiments prescribed by the Association for Research in Vision and Ophthalmology together with the guidelines from the Ministry of Food and Drug Safety (MFDS). This has been done in compliance with the relevant guidelines. The protocols were reviewed and approved by the Institutional Animal Care and Use Committee (IACUC) of the Asan Institute for Life Sciences in Asan Medical Center (Permit Number: 2016-13-182). All rats were maintained in the specific pathogen-free (SPF) facility at the Disease-focused Animal Resource Center in Asan Medical Center.

<2-2> Production of Pde6b-Deficient Rats

Pde6b-deficient rat embryos were produced by microinjection and used to produce mutant rats via foster mothers.

Specifically, as wild-type rats for the production of mutant rats, Sprague Dawley (SD) rats were purchased from OrientBio as embryo donors and foster mothers. The purchased rats were acclimatized to a breeding environment, and then the 5- to 6-week-old female rats were intraperitoneally injected with 40 IU pregnant mare serum gonadotropin (PMSG, Sigma). Then, superovulation was induced by injecting 40 IU human chorionic gonadotropin (hCG, Sigma) at 48-hour intervals. The superovulation-induced female rats were crossed with SD stud male rats, and fertilized eggs were obtained from the oviducts. When the fertilized egg (embryo) obtained was at the pronuclear stage, 100 ng/ml of crRNA and 50 ng/ml of Cpf1 mRNA prepared in Example <1-1> were microinjected into the cytoplasm of the embryo. The microinjected embryo was caused to migrate into the oviduct of a pseudo-pregnant foster mother, so that the embryo was induced to implant in the uterus.

Cells were obtained from the implanted embryo, and PCR was performed using the primer pairs prepared in Example <1-2> to identify the presence of Pde6b mutant founder. FIG. 3A illustrates results of PAGE-based genotyping assay which identifies founder rats originating from embryos at the pronuclear stage into which Cpf1 mRNA and its cognate crRNA targeting the rat Pde6b locus have been intracytoplasmically injected. As illustrated in FIG. 3A, it was identified that Pde6b mutant founders of #26 and #33 are obtained, and it was identified, through sequencing thereof, that each Pde6b mutant founder has an out-of-frame mutation (FIG. 3B). In FIG. 3B, the target sequence is underlined and PAM is boxed. "-" represents a deleted nucleotide. FIG. 3C illustrates representative PCR genotyping results that determine wild type, heterozygous mutant and homozygous mutant progeny of F0 #33.

The respective mutant rats were crossed with wild-type rats to produce F1 rats. Among these, the mutant rats obtained were sequenced again to identify that the allele of the mutant identified in the founder was germline transmitted.

<2-3> Establishment of Pde6b Knockout Rat Lines

In order to establish Pde6b knockout rat lines, mutant rats of founders with desired knockout alleles were crossed with wild-type SD rats, and the F1 heterozygotes were screened and sequenced. After breeding heterozygous knockout rats by crossing with wild-type SD rats, homozygous Pde6b knockout rats were generated by crossing male and female heterozygotes. For routine PCR genotyping, a primer pair that produced a short PCR product (173 bp in the wild-type mouse) was used to detect deletion with a frameshift mutation in the knockout allele.

In the examples below, the retina of F2 and F3 generation rats was examined morphologically and functionally for signs of pathological changes.

Example 3

Identification of Expression of Pde6b Protein in Retina of Pde6b Knockout Rats

Western blot was performed as follows to identify the expression of the Pde6b protein in the retina of the Pde6b KO rats produced in Example <2-2>.

Whole eyes were homogenized in lysis buffer (50 mM Tris, 100 mM NaCl, 5 mM EDTA, 0.1% SDS, 1% Triton X-100, 2.5% glycerol) supplemented with complete protease inhibitor cocktail (Roche Applied Science, Indianapolis, Ind., USA). The samples were cooled for 30 minutes on ice at −4° C. and then centrifuged at 13,000 g for 15 minutes at 4° C. Then, the supernatant was collected. Equal quantities of 35 µg of each sample were resolved by electrophoresis in a running buffer on 10% sodium dodecyl sulfate polyacrylamide (SDS-PAGE) gel. Samples were electrophoretically transferred to a polyvinylidene fluoride membrane (PVDF) (Bio-Rad Laboratories, Hercules, Calif., USA), which was blocked in Tris-buffered saline with Tween 20 (TBST) (10 mM Tris pH 8.0, 150 mM NaCl, 0.2% Tween 20). The PVDF membrane containing the transferred proteins was blocked with 5% lyophilized skim milk in PBS for 1 hour at room temperature. After overnight incubation with a primary antibody against Pde6b (Santa Cruz Biotechnology, Santa Cruz, Calif., USA), the membranes were washed with TBST and subsequently incubated with anti-mouse peroxidase-linked secondary antibodies (Amersham Pharmacia, Baie d'Urf'e, QC, Canada). Detection of protein signals was performed by using a chemiluminescent reagent (SuperSignal West Dura Extended Duration Substrate; Thermo Fisher Scientific, Fairlawn, N.J., USA), and then membranes were exposed to autoradiography imaging film (X-OMAT; Eastman Kodak, Rochester, N.Y., USA). In order to ensure equal protein loading, the same blot was subsequently incubated with an a-tubulin antibody (Cell Signaling Technology, Danvers, Mass., USA).

As a result, as identified in FIG. 4, expression of Pde6b was not detected in the wild-type and Pde6b knockout rats until 1 week of postnatal age, and the Pde6b protein was detected only in the wild-type rats even after 2 weeks of postnatal age.

Example 4

Identification of retinal degeneration in Pde6b-deficient rats

<4-1> Fundus Photography

In order to identify whether the Pde6b-deficient rats produced in the present invention can be used as an animal model of retinal degeneration, general findings of the retina were checked.

Specifically, using two male and two female Pde6b KO rats produced in Example <2-2> as an experimental group, fundus photography was performed at 1 day and 8 weeks of postnatal age. The eyes of Pde6b KO rats were anesthetized with a topical anesthetic, and pupillary dilatation was induced with eye drops containing 5 mg/ml of tropicamide and 5 mg/ml of phenylephrine HCl. An ophthalmic artificial tear ointment was used to prevent drying of the cornea during fundus photography. Retinal photographs were taken with the Micron IV fundus camera (Phoenix Research Laboratories, Pleasanton, Calif., USA). All taken fundus images were stored and data processed using the Micron IV software (StreamPix; NorPix, Inc., Montreal, QC, Canada). As a normal control, for one male and one female normal rats, fundus photography was performed in the same manner at 1 day and 8 weeks of postnatal age.

Figure 5:
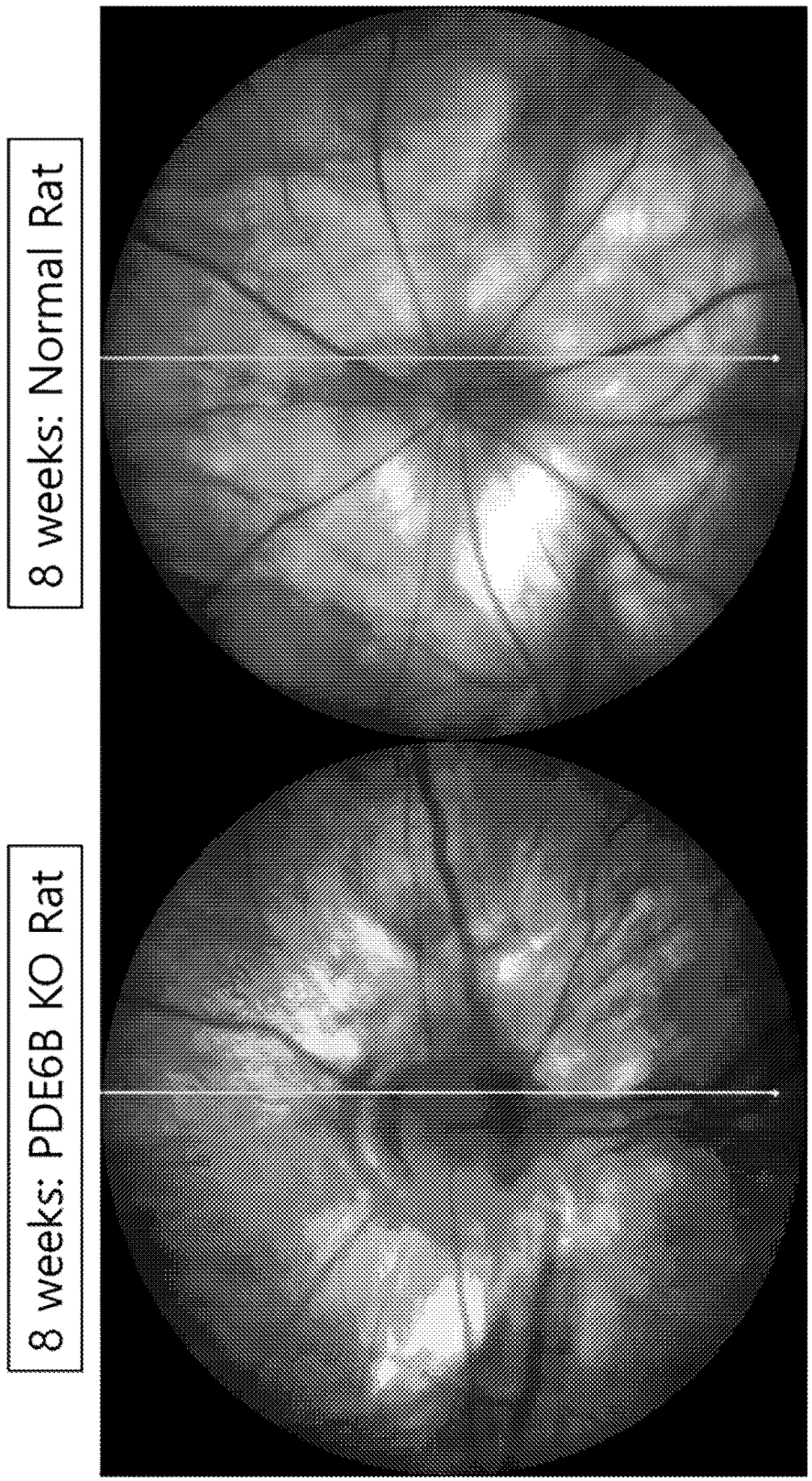
FIG. 5 illustrates fundus photographic images for Pde6b-deficient rats.

As a result, as illustrated in FIG. 5, it was identified that according to the fundus photographic findings, 8-week-old Pde6b KO rats exhibit an irregular pattern in retinal vascular morphology radially traveling around the optic nerve, as compared with the normal control (FIG. 4).

<4-2> Optical Coherence Tomography

In order to identify whether the Pde6b-deficient rats produced in the present invention can be used as an animal model of retinal degeneration, findings of the retina single-layer were checked by spectral-domain optical coherence tomography (SD-OCT).

Specifically, using two male and two female Pde6b KO rats produced in Example <2-2> as an experimental group, optical coherence tomography (Phoenix Research Labs) was performed at 1 day, 3 weeks, and 8 weeks of postnatal age. The retinal single-layer was scanned six times in a repeated manner, and the resulting values were averaged to acquire an image. The acquired images were output in tagged image file (.tif) format, and retinal thickness and retinal pigment epithelium, outer nuclear layer, outer plexiform layer, inner nuclear layer, inner plexiform layer, and the like were compared. As a normal control, for one male and one female normal rats, optical coherence tomography was performed in the same manner at 1 day, 3 weeks, and 8 weeks of postnatal age.

Figure 6:
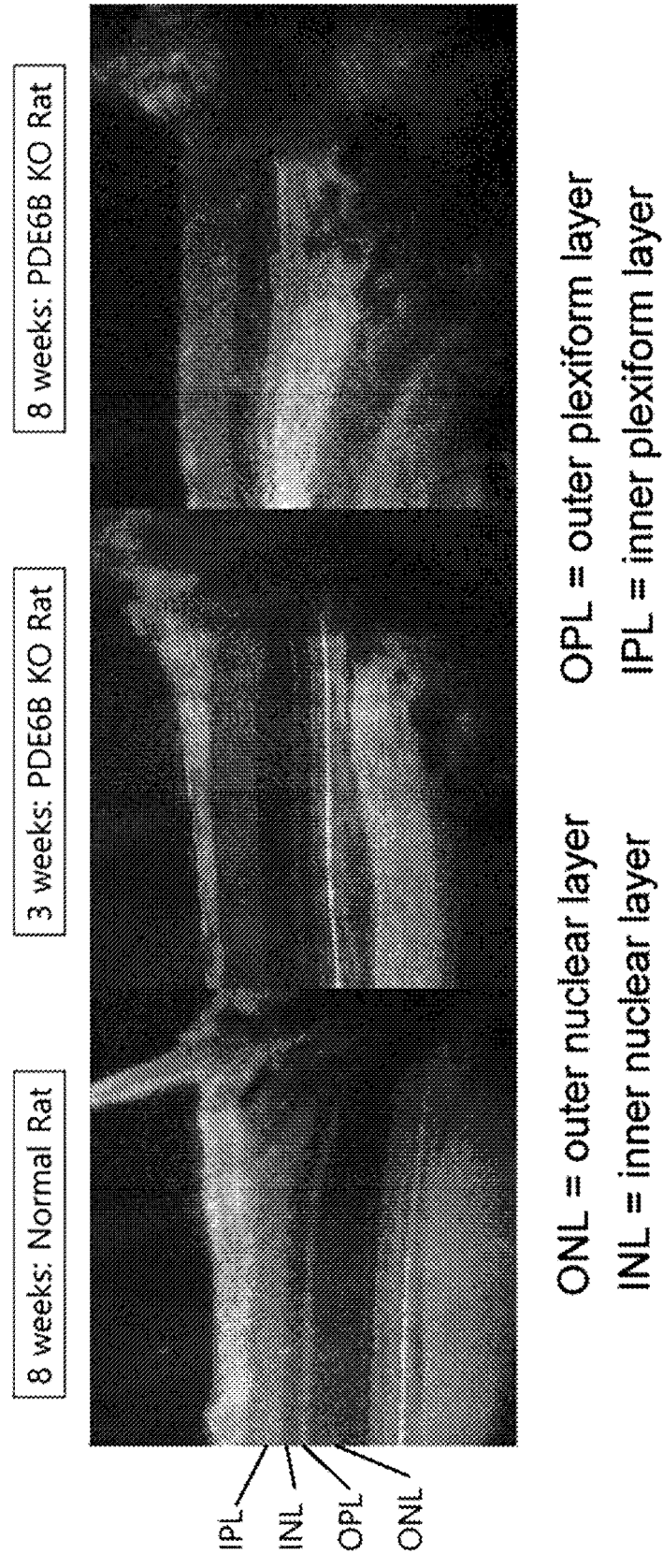
FIG. 6 illustrates optical coherence tomographic images for Pde6b-deficient rats.

As a result, as illustrated in FIG. 6, it was identified that the three-week-old Pde6b KO rats clearly show a decrease in overall retinal thickness and loss of the photoreceptor layer and the outer nuclear layer. The eight-week-old Pde6b KO rats showed the findings that along with the outer nuclear layer and the outer plexiform layer, the retinal pigment epithelium adjacent thereto is also lost.

<4-3> Electroretinograms

In order to identify whether the Pde6b-deficient rats produced in the present invention can be used as an animal model of retinal degeneration, electroretinograms were performed.

Specifically, using two male and two female Pde6b KO rats produced in Example <2-2> as an experimental group, electroretinograms were performed on 1-day-old, 3-week-old, and 8-week-old rats. Each rat in the experimental group was dark-adapted for 12 hours or longer before the electroretinograms, and prepared for electroretinogram measurement under a dark environment with illuminance ($\lambda$) of less than 600 nm. After the preparation, each rat in the experimental group was anesthetized by intraperitoneal injection of Zoletil® (125 mg/ml of Tiletamine and 125 mg/ml of Zolazepam, Virbac, France) at a dose of 0.01 ml. In addition, the pupils were dilated by the application of Midrin®-P eye drop (5 mg/ml of phenylephrine hydrochloride and 5 mg/ml of tropicamide, Santen, Japan). In addition, Alcaine® (0.5% proparacaine hydrochloride, Alcon Laboratories Inc.) was applied for ocular anesthesia. The anesthetized rat was stably fixed on a support for experimental animals so that its position was maintained for highly-reproducible electrophysiological tests.

Electroretinograms were performed using the Ganzfeld ERG system (Phoenix Research Labs) with light stimulus and electrical signal measurement. Electroretinogram signals were measured using the right eye of the experimental rat, and the electrical signals were sequentially measured while increasing the intensity of white light. Light exposure time was set to 10 msec, and the electric signal was recorded using an average value of 10 measurements at each light intensity. Corneal electrodes made of pure gold were placed around the cornea. Reference electrodes were placed in the center of the scalp; and ground leads were placed in the skin at the base of the tail. In addition, in order to identify the function of each of the retina's rod cells and cone cells, dark- and light-adapted a-wave and b-wave responses were checked. As a normal control, for one male and one female normal rats, electroretinograms were performed in the same manner at 1 day, 3 weeks, and 8 weeks of postnatal age.

Figure 7:
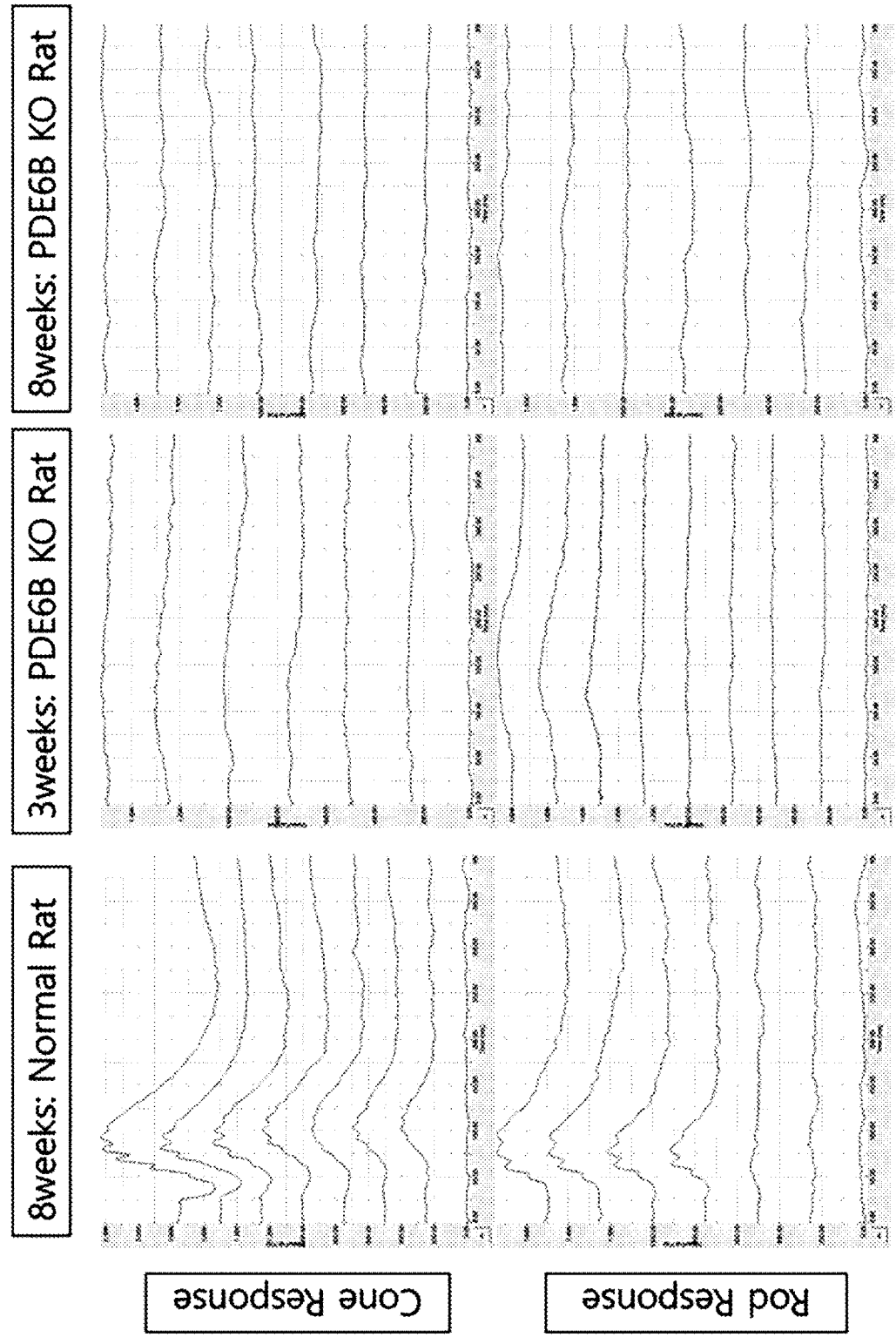
FIG. 7 illustrate electroretinogram results for Pde6b-deficient rats.

As a result, as illustrated in FIG. 7, in the electrophysiological tests using white light, it was identified that the dark- and light-adapted a-wave and b-wave responses identified in normal individuals are not observed in 8-week-old Pde6b-deficient rats and these rats show flat patterns.

<4-4> Identification of Histochemical Pathological Findings

In order to identify whether the Pde6b-deficient rats produced in the present invention can be used as an animal model of retinal degeneration, eye tissues were fixed to prepare samples and histochemical observations were performed thereon.

Specifically, using two male and two female Pde6b KO rats produced in Example <2-2> as an experimental group, histochemical pathological findings were identified on 1-day-old, 3-week-old, and 8-week-old rats. The experimental rats were anesthetized by intraperitoneal injection with 0.01 ml of Zoletil® (125 mg/ml of Tiletamine and 125 mg/ml of Zolazepam, Virbac, France). Then, the eyes were extracted and fixed in a 4% paraformaldehyde solution (pH 7.4). The fixed eye was dissected around the optic nerve, embedded in paraffin, cut into 4 μm thicknesses, and subjected to H & E staining (hematoxylin-eosin staining) to prepare histochemical samples. Histopathological findings were identified by comparing the prepared tissue samples with those of a normal control. As the normal control, for one male and one female normal rats, histopathological findings were identified in the same manner at 1 day, 3 weeks, and 8 weeks of postnatal age.

As a result, as illustrated in FIGS. 8A to 8D, it was identified that histochemical changes in the retina are observed over time in the PED6B KO rats.

Figure 8A:
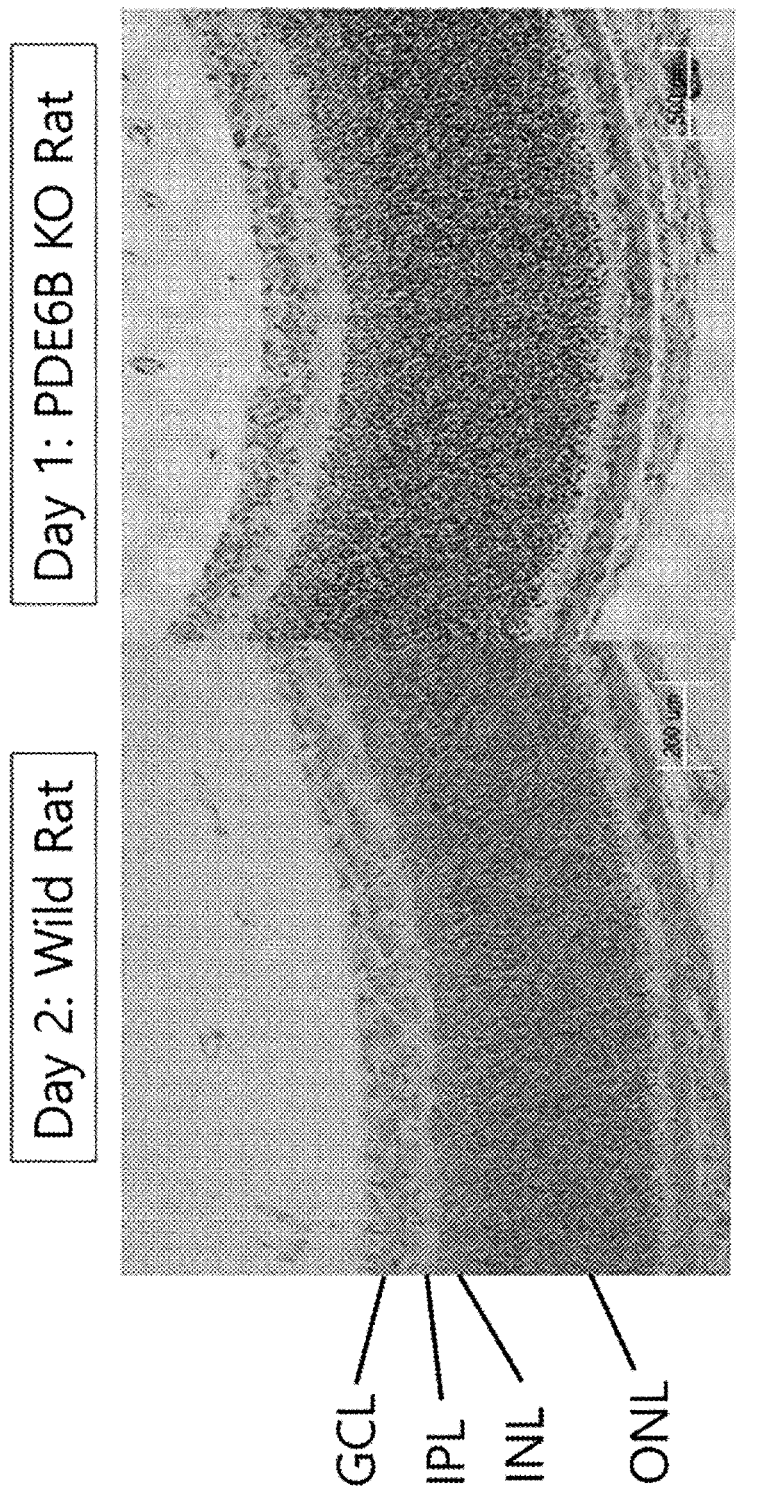
FIGS. 8A to 8D illustrate results obtained by observing, with histochemical analysis, the eye tissue of Pde6b-deficient rats.

First, it was identified that in both the normal control and the experimental group at 1 day of postnatal age, the outer nuclear layer and the inner nuclear layer are not distinguished from each other and are clustered together, and decreased thickness and loss of the outer nuclear layer thickness are not clearly observed (FIG. 8A).

Figure 8B:
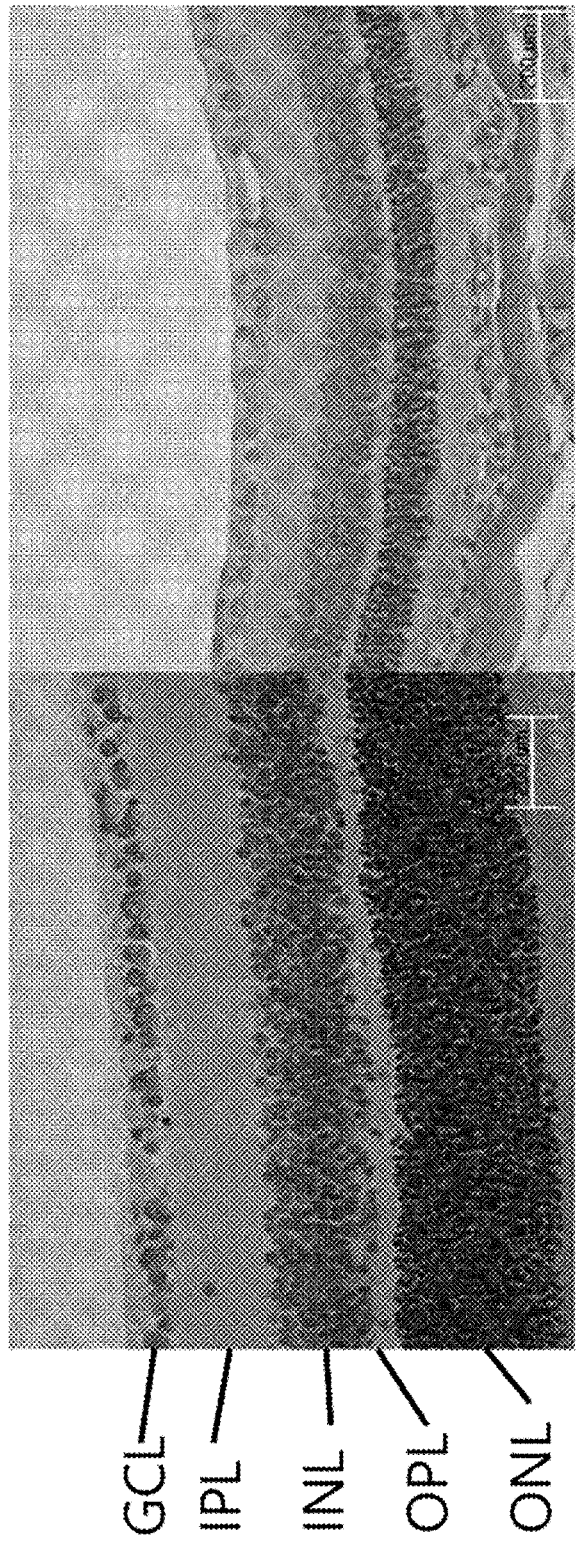

For the 3 week-old rats, it was identified that in the normal control, the outer nuclear layer and the inner nuclear layer have been developed in a separated state; however, in the Pde6b KO experimental group, the thickness of the outer nuclear layer is generally thinner than the normal control, and the cell density is also not higher than the normal control (FIG. 8B).

Figure 8C:
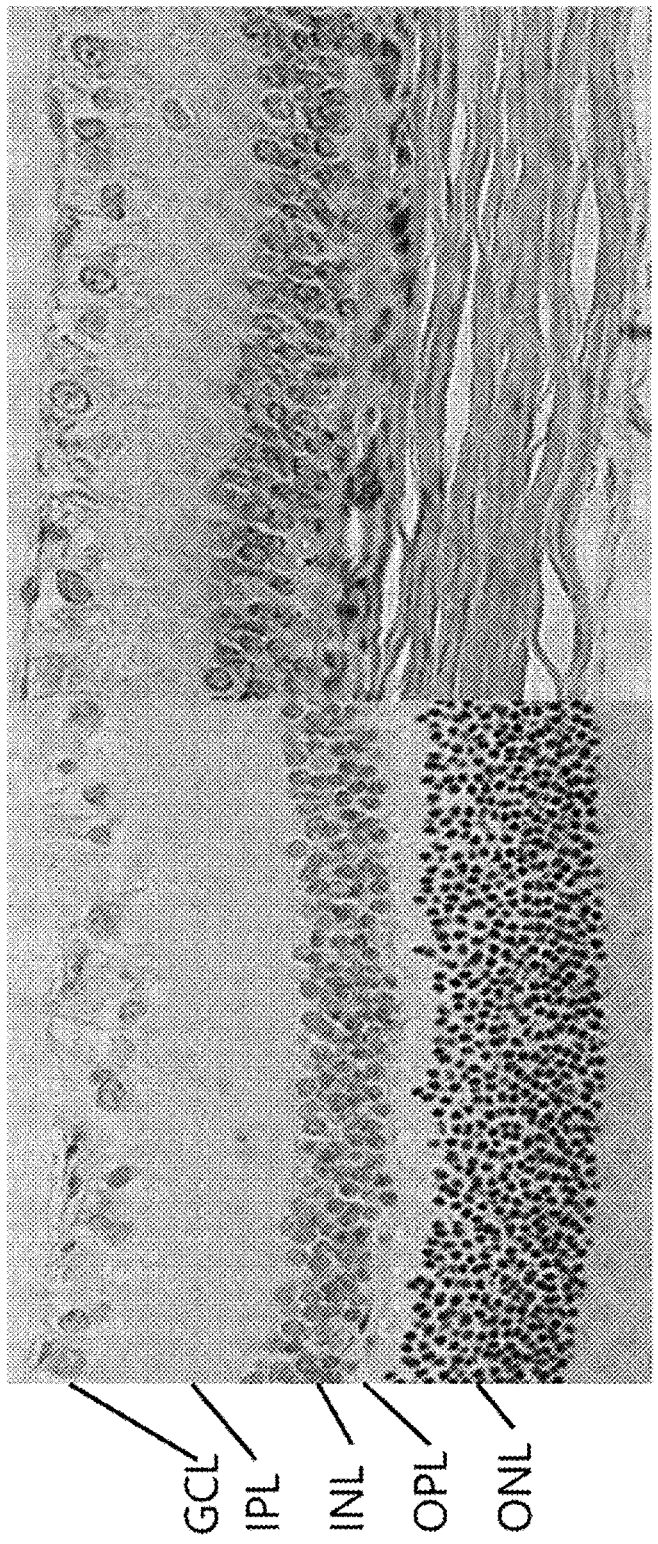

For the 8-week-old rats, it was identified that the retinal thickness decreases due to complete disappearance of the outer nuclear layer in the Pde6b KO experimental group, as compared with the normal control, and that they show the findings that the outer nuclear layer and the outer plexiform layer have completely disappeared from the fact that the adjacent inner nuclear layer exhibits a large and somewhat irregular nuclear shape (FIG. 8C).

Figure 8D:
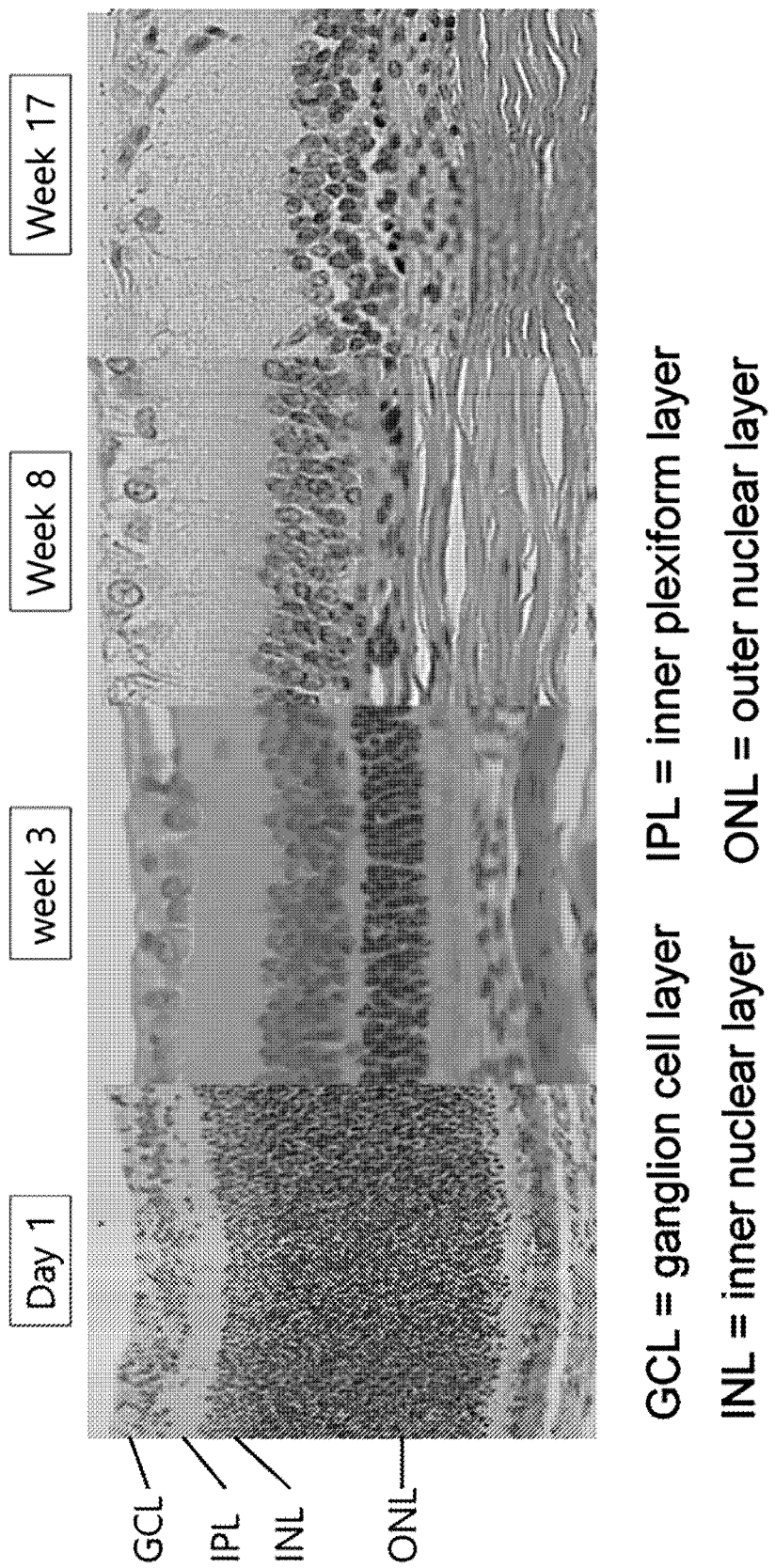

In a case where morphological changes in the retina are compared over time until 17 weeks of postnatal age, it was identified that in the Pde6b KO experimental group, the cell number in the outer nuclear layer decreases starting from 3 weeks of postnatal age and the outer nuclear layer has been completely lost at 8 weeks of postnatal age (FIG. 8D). It was identified that since then, similar trends have continued without any significant difference until 17 weeks of postnatal age, which identifies that the Pde6b-deficient rats of the present invention can be stably used as an animal model of retinal degeneration.

Example 5

Measurement of Photoreceptor Apoptosis Using TUNEL Assay

Photoreceptor apoptosis was determined by using the terminal deoxynucleotide transferase nick-end labeling (TUNEL) assay with the DeadEnd Fluorometric TUNEL System (Promega, Madison, Wis., USA). For TUNEL, sections were deparaffinized, rehydrated, treated with Proteinase K, reacted with TdT/nucleotide mix (containing fluorescein-12-dUTP), and counterstained with DAPI-blue. All samples were examined on the Zeiss LSM 780 confocal microscopy system (Carl Zeiss Meditec AG, Jena, Germany). The TUNEL-positive nuclei within a section of the superior and inferior retina 500 to 750 μm from the optic disc were compared between Pde6b knockout rats (two males, two females) and age-matched wild-type rats (one male, one female) at each time point.

Figure 9:
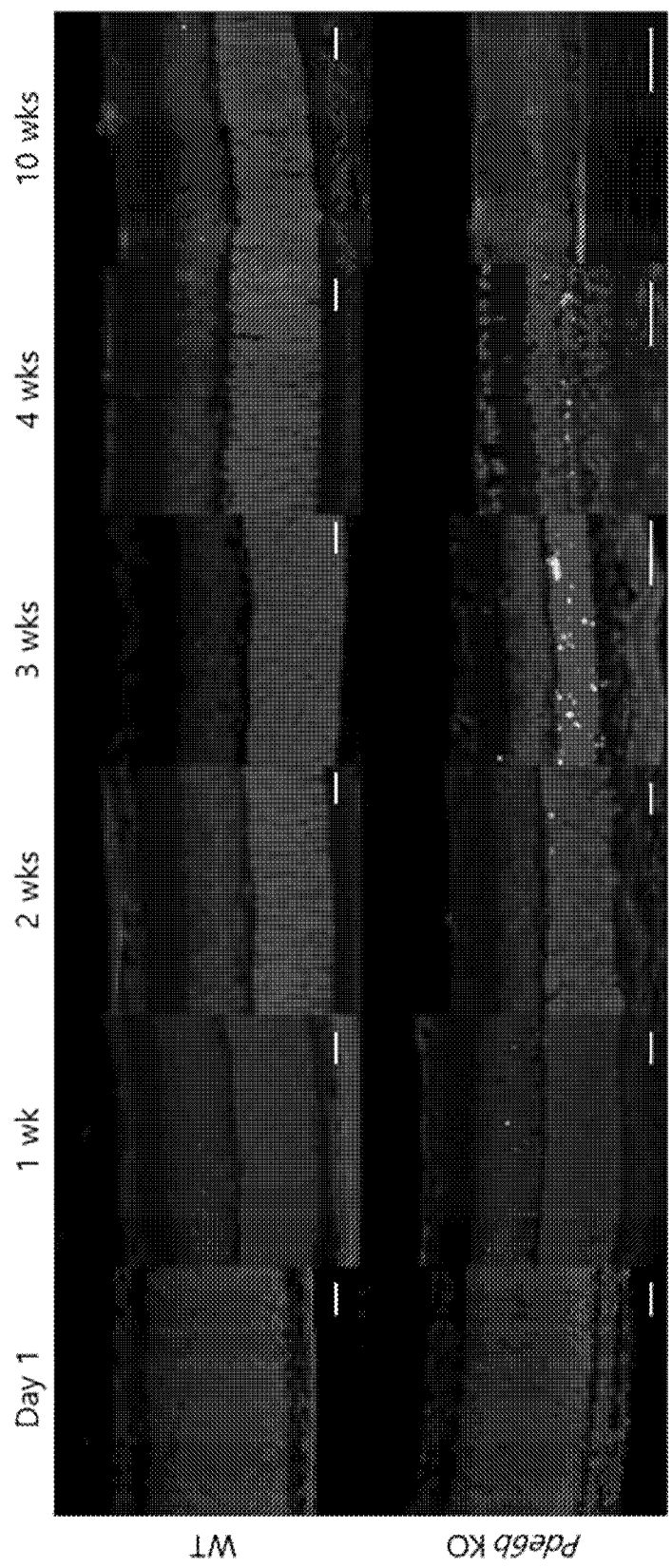
FIG. 9 illustrate TUNEL staining results for wild-type rats and Pde6b knockout rats at each time point (scale bars: 50 μm).

As a result, as illustrated in FIG. 9, the retinal tissue sections of the Pde6b knockout rats showed TUNEL-positive findings which are not seen in the wild-type rats (TUNEL-positive cells show yellow-green). Apoptosis began 2 weeks of postnatal age, reached its peak at 3 weeks of postnatal age, and then decreased. Signals were specific in the outer nuclear layer and little or no signal was observed in the inner nuclear layer. On the contrary, the wild-type rats showed very little signal in the inner nuclear layer at 1 to 10 weeks of postnatal age.

From the above results, it was identified that the Pde6b knockout rats of the present invention can be stably used as an animal model of retinal degeneration.

What is claimed is:

1. A method for producing a genetically modified rat model of retinal degeneration, the method comprising:
   a) generating CRISPR RNA (crRNA) that targets a rat PDE6B gene and mRNA encoding CPF1 endonuclease;
   b) injecting the crRNA and mRNA into a rat embryo; and
   c) implanting the embryo into a foster mother such that a rat comprising germline cells whose genomes comprise an inactivated PDE6B gene is obtained;
   d) crossing the rat obtained in step c) with a wild-type rat such that a genetically modified rat whose genome comprises a heterozygous inactivated PDE6B gene is obtained;
   e) crossing the rat obtained in step d) with a littermate such that a genetically modified rat whose genome comprises a homozygous inactivated PDE6B gene with increased susceptibility to retinal degeneration is obtained.

2. The method according to claim 1, wherein the genetically modified rat obtained in step e) displays retinitis pigmentosa, an angioid streak, drusen, or macular degeneration.

3. A genetically modified rat whose genome comprises a homozygous inactivated PDE6B gene obtained by the method of claim 1, wherein the rat has increased susceptibility to retinal degeneration as compared to a wild-type rat or has retinal degeneration.

4. The genetically modified rat of claim 3, wherein the rat displays retinitis pigmentosa, an angioid streak, drusen, or macular degeneration.

5. A method of screening for a drug that prevents retinal degeneration, the method comprising:
   a) administering a drug to a genetically modified rat whose genome comprises an inactivated PDE6B gene obtained by the method of claim 1, wherein the rat has increased susceptibility to retinal degeneration as compared to a wild-type rat; and
   b) determining whether the drug prevents onset of retinal degeneration in the rat as compared to a genetically modified rat whose genome comprises a homozygous inactivated PDE6B gene not given the drug.

6. The method according to claim 5, wherein the determining comprises evaluating retinal vascular morphology, retinal monolayer thickness, electroretinogram amplitude, or cell number in retinal tissue.

7. The method according to claim 5, wherein the genetically modified rat displays retinitis pigmentosa, an angioid streak, drusen, or macular degeneration.

8. A method of screening for a drug that treats retinal degeneration, the method comprising:
   a) administering a drug to a genetically modified rat whose genome comprises a homozygous inactivated PDE6B gene obtained by the method of claim 1, wherein the rat displays retinal degeneration; and
   b) determining whether the drug treats the retinal degeneration in the rat as compared to a genetically modified rat whose genome comprises a homozygous inactivated endogenous PDE6B gene not given the drug.

9. The method according to claim 6, wherein the determining comprises evaluating retinal vascular morphology, retinal monolayer thickness, electroretinogram amplitude, or cell number in retinal tissue.

10. The method according to claim 8, wherein the genetically modified rat displays retinitis pigmentosa, an angioid streak, drusen, or macular degeneration.

* * * * *